United States Patent
Ottens et al.

(10) Patent No.: US 6,456,375 B1
(45) Date of Patent: Sep. 24, 2002

(54) FOCUSED LASER LIGHT TURBIDITY SENSOR APPARATUS AND METHOD FOR MEASURING VERY LOW CONCENTRATIONS OF PARTICLES IN FLUIDS

(75) Inventors: Gregory J. Ottens, Freeport, IL (US); Kevin J. Engler, Freeport, IL (US); Thomas R. Guiffre, Freeport, IL (US); Thomas M. Moyer, Freeport, IL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/788,724

(22) Filed: Feb. 20, 2001

(51) Int. Cl.[7] .......................... G01N 21/00; G01N 15/06
(52) U.S. Cl. ...................... 356/339; 356/343; 250/574
(58) Field of Search ................................. 356/335–343, 356/440, 432, 436; 250/573, 574, 576

(56) References Cited

U.S. PATENT DOCUMENTS

| | | |
|---|---|---|
| 3,713,743 A | 1/1973 | Simms |
| 3,880,526 A | 4/1975 | Kobayashi et al. |
| 4,152,070 A | 5/1979 | Kushner et al. |
| 4,193,692 A | 3/1980 | Wynn |
| 4,198,161 A | 4/1980 | Larson ........................ 356/339 |
| 4,263,511 A * | 4/1981 | Hirschberg ................. 356/343 |
| 4,497,577 A * | 2/1985 | Sato et al. .................... 356/336 |
| 4,999,514 A | 3/1991 | Silveston |
| 5,012,119 A | 4/1991 | Rhiner |
| 5,025,169 A | 6/1991 | Arakawa et al. |
| 5,140,168 A | 8/1992 | King |
| 5,291,626 A | 3/1994 | Molnar et al. ................. 8/158 |
| 5,331,177 A | 7/1994 | Kubisiak et al. |
| 5,408,307 A | 4/1995 | Yamamoto et al. |
| 5,444,531 A | 8/1995 | Foreman et al. |
| 5,446,531 A | 8/1995 | Boyer et al. |
| 5,485,013 A | 1/1996 | Cummins |

(List continued on next page.)

FOREIGN PATENT DOCUMENTS

| | | |
|---|---|---|
| DE | 296 22 293 U | 3/1997 |
| DE | 198 06 559 A | 8/1999 |
| WO | WO 99 36772 A | 7/1999 |

OTHER PUBLICATIONS

PCT International Search Report, dated Mar. 4, 2002, relevant to PCT counterpart of current U.S. patent application.

Primary Examiner—Hoa Q. Pham
(74) Attorney, Agent, or Firm—Andrew A. Abeyta; Kermit Lopez; Luis M. Ortiz

(57) ABSTRACT

A turbidity sensor apparatus and method for measuring very low concentrations of particles in a fluid. The turbidity sensor comprises a laser light source for emitting laser light through a fluid. Such a fluid may be hydraulic fluid, oil, water utilized in water purification systems, or other translucent fluids. The turbidity sensor includes a first light-sensitive detector located 90 degrees to incident laser light emitted from the laser light source, and a second light-sensitive detector located at an angle obtuse to the incident laser light emitted from the laser light source, wherein the first and second light-sensitive detectors respectively measure side scattered light and forward scattered light reflected from particles contained within the fluid that come into contact with laser light emitted from the laser light source, thereby providing an accurate and reliable measurement of very low concentrations of particles within the fluid. The turbidity sensor also includes a component for capturing incident laser light entirely emitted from the laser light source, thereby preventing reflection of the laser light back into the fluid. The laser light source may be a Vertical Cavity Surface Emitting Laser (VCSEL) or other light emitting light source.

20 Claims, 6 Drawing Sheets

U.S. PATENT DOCUMENTS

| | | | |
|---|---|---|---|
| 5,489,977 A | 2/1996 | Winslow | |
| 5,565,984 A | 10/1996 | Girvin | |
| 5,589,935 A | 12/1996 | Biard et al. | 356/339 |
| 5,596,408 A | 1/1997 | Cummins et al. | |
| 5,603,233 A | 2/1997 | Erickson et al. | |
| 5,604,590 A | 2/1997 | Cooper et al. | |
| RE35,566 E | 7/1997 | Boyer et al. | |
| 5,729,025 A | 3/1998 | Erickson et al. | 250/574 |
| 5,757,481 A | 5/1998 | O'Brien et al. | |
| 5,793,485 A * | 8/1998 | Gourley | 356/318 |
| 5,800,628 A | 9/1998 | Erickson et al. | |
| 5,828,458 A | 10/1998 | Taylor et al. | 356/440 |
| 5,872,361 A | 2/1999 | Paoli et al. | 250/341.8 |
| 5,881,578 A | 3/1999 | Proppe et al. | 68/12.02 |
| 5,889,192 A | 3/1999 | Engel | 73/1.02 |
| 5,906,802 A | 5/1999 | Langford | |
| 5,923,433 A | 7/1999 | Giuffre et al. | 356/440 |
| 5,957,144 A | 9/1999 | Neff et al. | 134/56 |
| 6,007,640 A | 12/1999 | Neff et al. | 134/18 |
| 6,052,184 A * | 4/2000 | Reed | 356/338 |
| 6,141,097 A | 10/2000 | Herman | 356/335 |

* cited by examiner

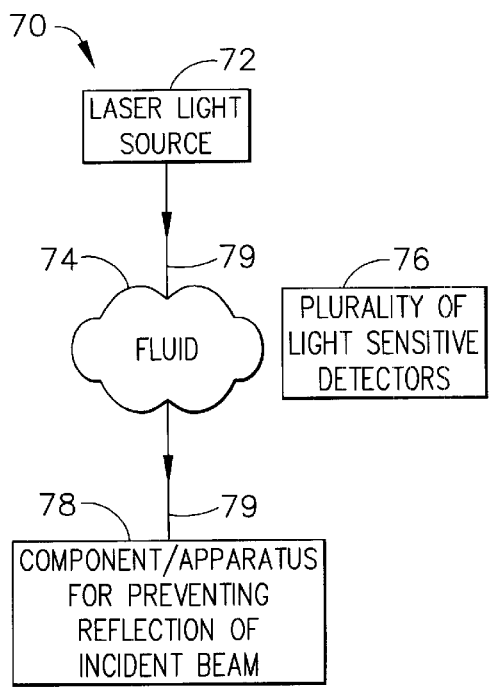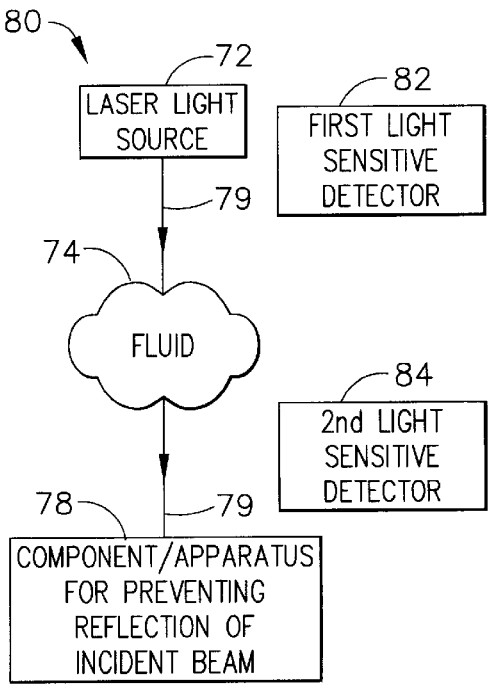
FIG. 3
FIG. 4
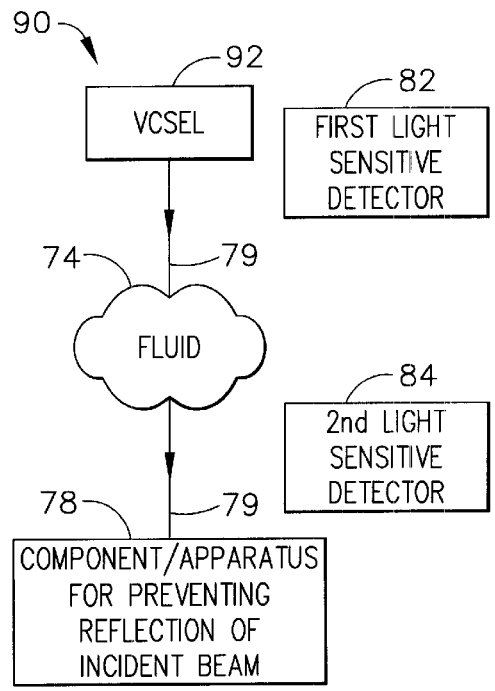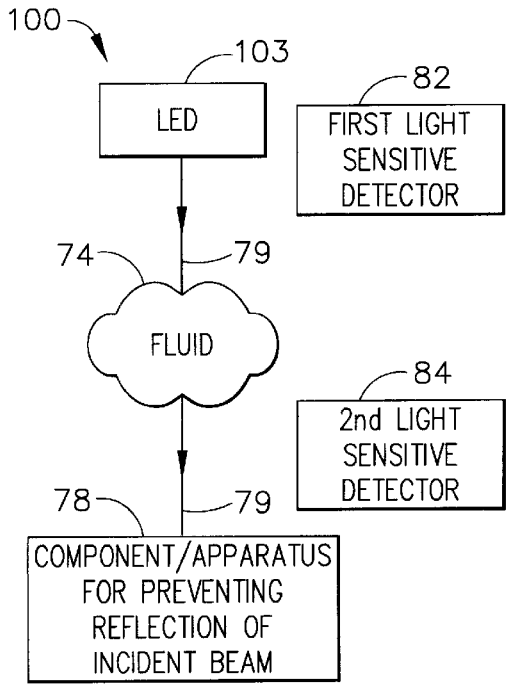
FIG. 5
FIG. 6

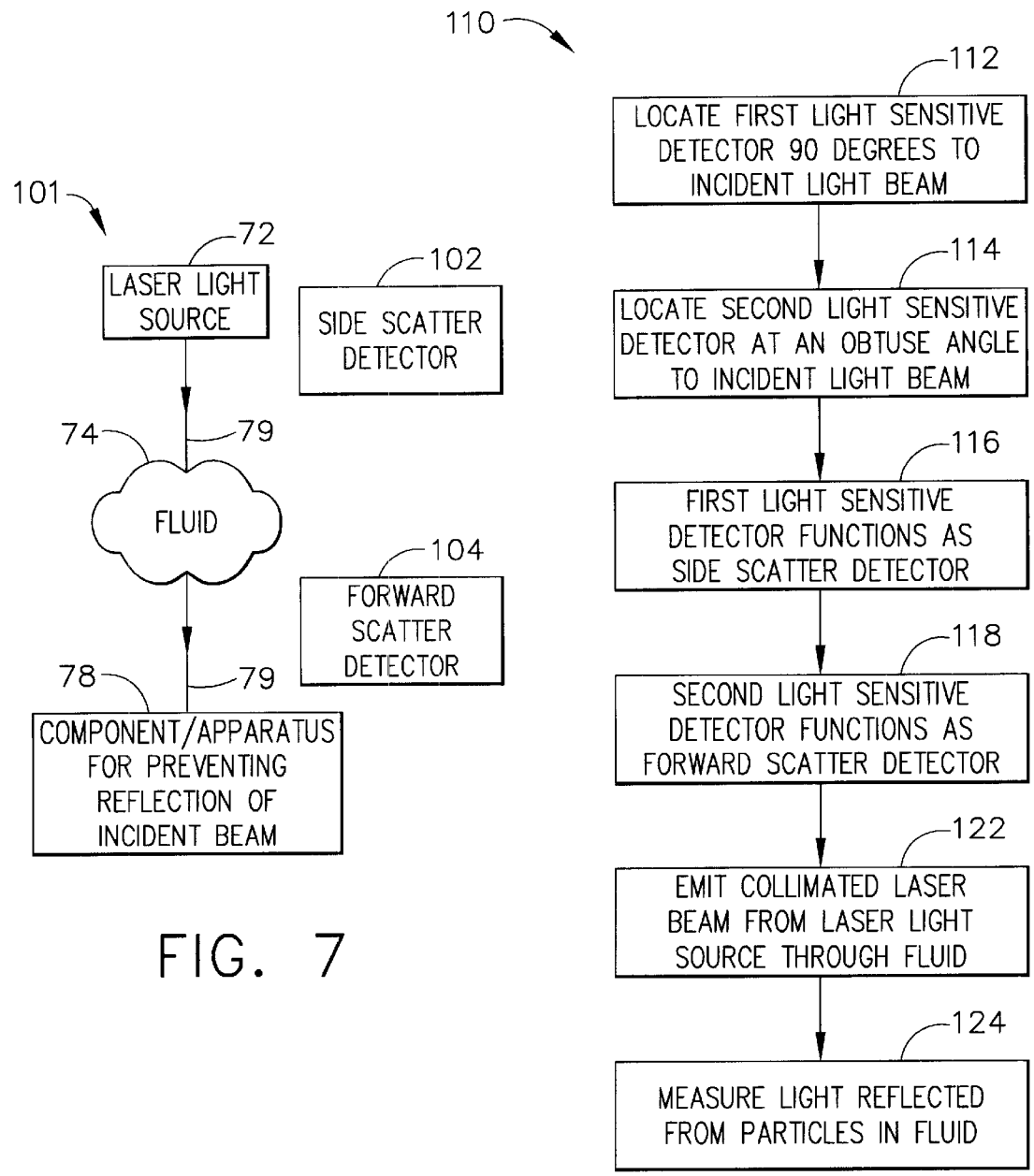

| NTU LEVEL | D-SIDE | FORWARD 1 | FORWARD 2 | FORWARD 3 | RAD. SIDE | BACK 3 | BACK 2 | BACK 1 |
|---|---|---|---|---|---|---|---|---|
| 0 | 0.002 | 0.027 | 0.010 | 0.004 | 0.003 | 0.003 | 0.005 | 0.011 |
| POTATO1 | 0.040 | 0.150 | 0.084 | 0.038 | 0.015 | 0.011 | 0.022 | 0.045 |
| POTATO2 | 0.020 | 0.140 | 0.062 | | 0.010 | | | 0.038 |

FOCUSED LASER LIGHT TURBIDITY SENSOR APPARATUS AND METHOD FOR MEASURING VERY LOW CONCENTRATIONS OF PARTICLES IN FLUIDS

This application is related to co-pending and co-owned patent applications entitled: "Focused Laser Light Turbidity Sensor," U.S. Ser. No. 09/788,723, filed on Feb. 19, 2001.

TECHNICAL FIELD

The present invention relates to sensor methods and systems. The present invention also relates to sensors that measure the turbidity and quality of fluid having particulate content therein. The present invention also relates to semiconductor-based sensors. The present invention additionally relates to photodiode-based sensors and methods thereof. The present invention also relates to laser emitting sensor devices and methods thereof. The present invention relates to turbidity sensors that monitor the status of a fluid and determine the presence or level of impurities in the fluid. The present invention also relates to techniques for measuring very low concentrations of particles in fluids.

BACKGROUND OF THE INVENTION

Reducing the amount of energy consumed by a machine for cleansing articles, such as a clothes washer, is a significant problem. In such a machine, the amount of energy consumed is primarily determined by the amount of energy needed to heat the liquid, such as water, used to cleanse the articles. Thus, decreased liquid consumption for such machines may result in a significant improvement in energy efficiency.

Appliances for cleansing articles, such as clothes washers, are typically preprogrammed to perform a complete washing in a predetermined number of wash cycles, each wash cycle having a predetermined duration. A wash cycle may provide substantially particle-free liquid to the machine, circulating the liquid during the wash cycle, and draining or flushing the liquid from the machine after being used to wash or cleanse the articles. Often the machine user may select from a limited number of preprogrammed options. Such preprogramming does not use energy efficiently because the machine may either perform an excessive number of wash cycles, or perform each cycle for an excessive duration, to assure that cleanliness of the articles is achieved. To improve the energy efficiency of such appliances, closed loop feedback control systems can be incorporated into the washing machine. Several techniques have been utilized to indirectly monitor cleanliness of the articles during closed loop feedback control of the appliance, including use of a device for measuring the turbidity of the liquid used to wash the articles.

Devices for measuring turbidity that detect the transmission of light propagated through water used to wash the articles have been employed to ascertain information about progress of the wash. However, such devices have not been ideal for use in household appliances. Such devices are oftentimes difficult or non-economic to implement due to the electronic circuitry necessary to perform the complex turbidity measurements. Furthermore, such devices are subject to measurement error. Factors such as water turbulence, cloudiness of the water sample chamber, light source dimming, or device performance degradation may cause attenuation of the amount of light detected and thus affect measurement accuracy. The precision of such devices is also not entirely satisfactory. This imprecision has the additional effect of making turbidity measurements provided by such devices difficult to interpret in a closed loop feedback control system.

Manufacturers of washing machines thus desire to control the washing algorithms with such machines in order to maintain high washability standards and increase energy efficiency. Turbidity measurement must be accurate over a broad range of washing cycles and turbid environments in order to make proper decisions during washing cycles.

Turbidity sensors can be utilized to monitor turbidity in liquids operating within turbid environments, such as a washing machine. Turbidity sensors monitor the status of a fluid and, more particularly, determine the presence or level of impurities in the fluid. Often the presence of impurities determines the suitability of the fluid for use in its intended purpose. As an example, lubricating oil having too high a contamination level should be cleansed or changed.

Turbidity sensors are thus utilized in many different types of applications, for example, in association with machines for washing articles, such as dishwashers and washing machines. Most turbidity sensors measure the effect on a light beam of particulate matter suspended within a fluid. Some turbidity sensors utilize only a transmitted light signal, while others utilize both scattered and transmitted light.

Certain prior art turbidity sensors operate by shining a light into a test cell that contains the fluid under scrutiny. The degree to which the light is transmitted as well as scattered gives an indication of the turbidity or pureness of the fluid sample. The previously known turbidity sensors often use light emitting diodes (LEDs) for light sources and the use of photodiodes and phototransistors for use as detectors to reduce costs. An output from such systems may employ light intensity to frequency converters. For example, a photodiode or phototransistor that monitors light intensity is coupled to such a converter to generate a signal whose frequency corresponds to and varies with the turbidity level of the fluid.

A problem identified in prior art turbidity sensors is that the light source that shines light into the fluid sample can change its emission characteristics with time or with variations in temperature. Similarly, changes in operating characteristics can take place in the sensors that are used to sense the light that travels through the fluid.

Prior art turbidity sensors have experienced problems when trying to sense the condition of fluids that are either at low or high turbidity levels. In addition, the sensor's test cell must be large enough to pass all suspended particles in the test material without fouling. The test cell must also be small enough, however, to allow light to be transmitted through the cell and received by a sensor on the opposite side of the test cell from the source. At high turbidity levels, a long transmission path will not pass enough light to allow the sensor to provide a meaningful measurement as the variation in light output such as a frequency. Conversely, at low turbidity levels, a test cell's transmission path may be too short to allow sufficient light to be scattered or absorbed to produce a meaningful measurement. The use of such test cells or sample cells is thus inefficient and difficult to implement.

Many fluid filters for liquids and gases function by particle entrapment. As filters gradually become clogged by the particles, detection of the need for cleaning or replacement is often accomplished by mass air flow measurements downstream of the filter, pressure drop measurements across the filter and motor or pump loading. All of these techniques have disadvantages in terms of cost, accuracy or reliability.

In addition, the structure and assembly of previously known turbidity sensors is often complex, particularly where the structure supports for the components are arranged to avoid improper alignments of the components with respect to each other. As a result, any supports for the components that are adjustable so as to permit a final alignment of the parts after assembly are quite complex and costly. Moreover, the previously known components and the support structures for the components are not well adapted for simple and economical mass production, and the assembly of products employing turbidity sensors that otherwise would be readily mass produced can be substantially complicated by installation of the previously known support structures and component assemblies. In addition, the performance of systems using light sensors can be substantially affected by temperature changes and component changes due to aging, contamination and the like.

The incorporation of turbidity sensors into a machine for washing articles, such as a washing machine or dishwasher, can increase the cost of the machine by a significant amount because of the complexity of such known turbidity sensors. Typically, a turbidity sensor can include a microprocessor, which controls the operation of the turbidity sensor and analyzes the signals received thereby to determine the magnitude of turbidity of the water within the machine for washing articles. It would be beneficial if the operation of a turbidity sensor could be significantly simplified and, as a result, the costs of the turbidity sensor significantly reduced.

One beneficial use to which a turbidity sensor can be applied is the conservation of water during the operation of a machine for washing articles. The repeated draining and refilling of a machine for washing articles uses a significant amount of water and, if it is not excessively dirty, the draining of the water can represent a significant waste of water. The appropriate use of a turbidity sensor can avoid the unnecessary draining and refilling of machines for washing articles.

There does not currently exist a low-cost method and device for sensing turbidity needed to measure very low concentrations of particulate in translucent fluids. In addition to utilizing turbidity sensors to assist in conserving water in devices such as washing machines, it is often necessary to measure extremely low levels of contaminants in water purification systems, hydraulic fluids, oils or other translucent fluids. In washing machines, for example, it is desirable to measure particles of extremely small size, such as dissolved starch, that have poor light-scattering properties. Such particles go undetected by current commercial methods of turbidity sensing, including devices and systems thereof.

A need thus exists for a device, including systems and methods thereof, for measuring turbidity in a simple and economic manner and which overcomes the aforementioned problems associated with prior art turbidity sensors. A need particularly exists for a turbidity sensor that overcomes the inability of prior art turbidity sensors to efficiently detect extremely low levels of particles in fluids. A low-cost sensing of turbidity is needed in a machine for washing articles where a full range of particulate content must be measured. In addition, accurate measurement of turbidity is needed in other applications, such as water quality systems, hydraulic oils, or any other application where fluid quality is measured.

BRIEF SUMMARY OF THE INVENTION

The following summary of the invention is provided to facilitate an understanding of some of the innovative features unique to the present invention, and is not intended to be a full description. A full appreciation of the various aspects of the invention can be gained by taking the entire specification, claims, drawings, and abstract as a whole.

It is one aspect of the present invention to provide sensor methods and systems.

It is another aspect of the present invention to provide a sensor that measures the turbidity and quality of fluids and viscous environments having particulate content.

It is also an aspect of the present invention to provide a semiconductor-based sensor.

It is an additional aspect of the present invention to provide photodiode-based sensor methods and systems.

It is another aspect of the present invention to provide laser emitting sensor devices and methods thereof.

It is still another aspect of the present invention to provide turbidity sensors that monitor the status of a fluid and determine the presence or level of impurities in the fluid.

It is yet another aspect of the present invention to provide techniques for measuring very low concentrations of particles in fluids.

The above and other aspects are achieved as is now described. A turbidity sensor apparatus and method for measuring very low concentrations of particles in a fluid are disclosed herein. The turbidity sensor is generally composed of a laser light source for emitting laser light through a fluid. Such a fluid may be hydraulic fluid, oil, water utilized in water purification systems, or other translucent fluids. The turbidity sensor includes a first light-sensitive detector located 90 degrees to incident laser light emitted from the laser light source and a second light-sensitive detector located at an obtuse angle to the incident laser light emitted from the laser light source, wherein the first and second light-sensitive detectors respectively measure side scattered light and forward scattered light reflected from particles contained within the fluid that come into contact with laser light emitted from the laser light source, thereby providing an accurate and reliable measurement of very low concentrations of particles within the fluid. The turbidity sensor also includes a component for capturing incident laser light entirely emitted from the laser light source, thereby preventing reflection of the laser light back into the fluid. The laser light source may be a Vertical Cavity Surface Emitting Laser (VCSEL) or other light emitting light source.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

FIG. 3 depicts a high-level block diagram illustrative of a focused laser turbidity sensor that includes a plurality of light-sensitive detectors, in accordance with preferred embodiments of the present invention;

FIG. 4 illustrates a high-level block diagram of a focused laser turbidity sensor that includes first and second light-sensitive detectors, in accordance with preferred embodiments of the present invention;

FIG. 5 depicts a high-level block diagram of a focused laser turbidity sensor that utilizes a Vertical Cavity Surface Emitting Laser (VCSEL) as a laser light source, in accordance with preferred embodiments of the present invention;

FIG. 6 illustrates a high-level block diagram of a focused laser turbidity sensor that utilizes a light emitting diode (LED) as a laser light source, in accordance with preferred embodiments of the present invention;

FIG. 7 depicts a high-level block diagram of a focused laser turbidity sensor that utilizes side scatter and forward scatter detectors, in accordance with preferred embodiments of the present invention;

FIG. 8 depicts a high-level flow chart of operations illustrating operational steps that may be implemented for measuring very low concentrations of particles in fluids, in accordance with preferred embodiments of the present invention;

DETAILED DESCRIPTION OF THE INVENTION

The particular values and configurations discussed in these non-limiting examples can be varied and are cited merely to illustrate an embodiment of the present invention and are not intended to limit the scope of the invention.

Figure 1:
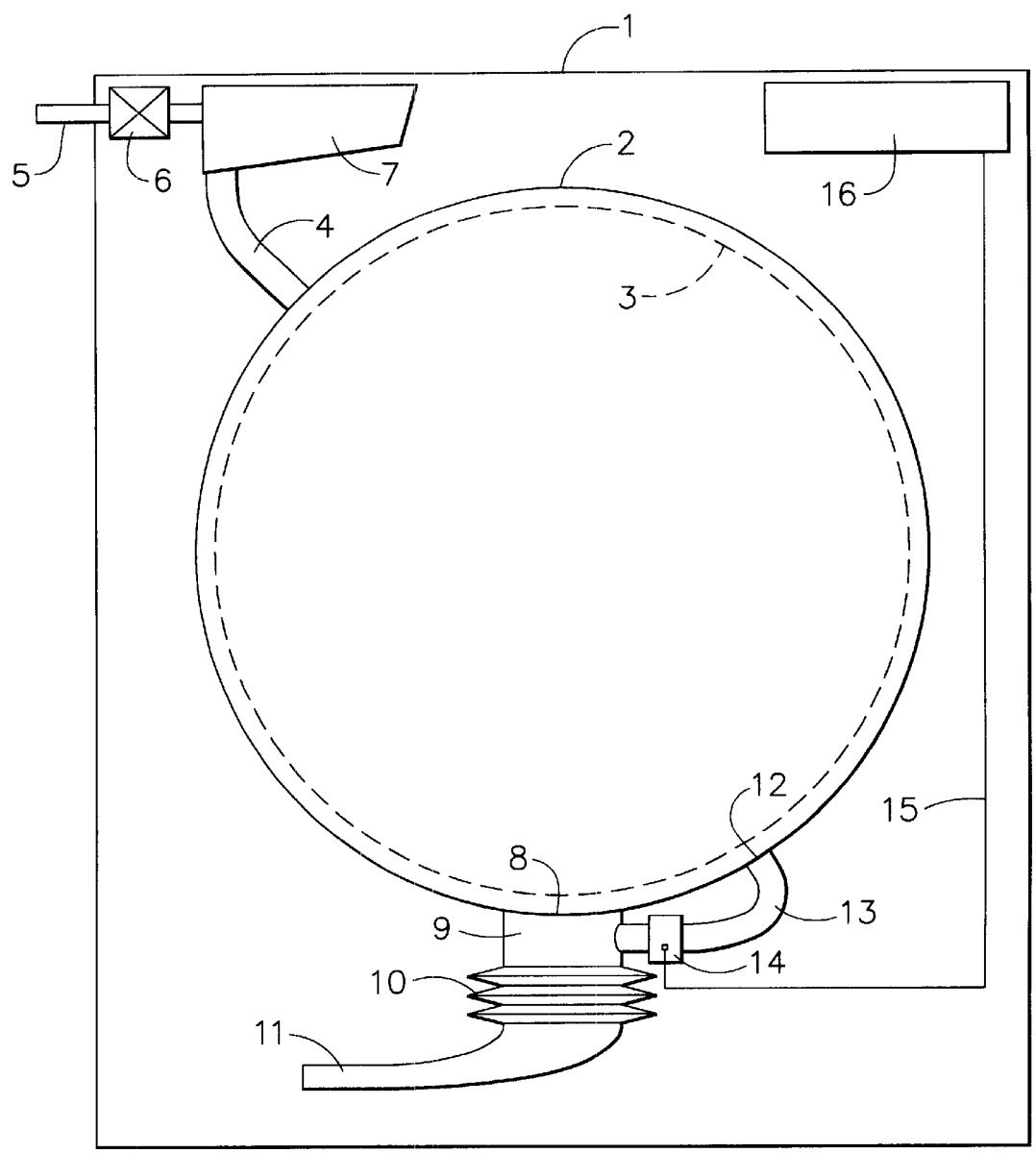
FIG. 1 is a schematic front view of a drum-type washing machine in which embodiments of the present invention may be implemented

FIG. 1 is a schematic front view of a drum-type washing machine in which a preferred embodiment of the present invention may be utilized. Those skilled in the art can appreciate that the drum-type washing machine illustrated in FIG. 1 represents one example of an environment in which the present invention described herein may be implemented. The present invention is not limited to washing machines, dishwashers and other such machines and environments, but may be implemented in any environment in which a need exists to measure the turbidity of fluids, including fresh water, salt water, viscous fluids, and other fluid environments.

The turbidity sensor described herein may be utilized to measure extremely low levels of contaminates in water purification systems, hydraulic fluids, oils, or other translucent fluids. Such a turbidity sensor can be utilized not only to measure very small concentrations of particles, but also to detect particles of extremely small size, such as dissolved starch, having poor light-scattering properties. The drum-type washing machine illustrated in FIG. 1 is thus presented for illustrative purposes only. It can be appreciated that the invention described herein may also be utilized for filtration, chemical processing, refining and other liquid based processes, wherein the drum-type system illustrated in FIG. 1 may be illustrative of a reservoir for various liquids.

The washing machine shown in FIG. 1 has a housing 1, in which a tub 2 (suds container) is mounted. While the specific details of the tub mounting are not illustrated, it is noted that the tub 2 is capable of vibrating. A laundry drum 3 is rotatably supported about a horizontal axis in the tub 2. Water and, optionally, detergent can be supplied to it in the upper portion of the tub 2 via a line 4 from a supply line 5 via a magnet valve 6 and a detergent dispenser 7. A drain line 9 communicates in fluid-tight fashion with a drain opening 8 in the lower portion of the tub 2. The drain line 9 communicates via bellows creases 10 and a further line 11, with a non-illustrated washwater pump fixedly mounted in the housing 1. Located between the drain line 9 and a further opening 12, which is disposed at a somewhat higher geodetic level than the drain opening 8, there is a line segment 13.

Due to the level difference between the openings 8 and 12, there is a steady flow of washwater through the line segment 13 during washing machine operation. The flow is thereby into and through the opening 12 to the drain line 9 and back via the drain opening 8 into the tub 2. As noted, the flow is based on the slight pressure differences in the washwater above the drain opening 8 and the opening 12. A sensor 14 may be mounted on the line segment 13, and its output signals are output via a line 15 to a processing and control unit 16. The unit 16 processes the sensor signals. Those skilled in the art can appreciate that there are many other physical locations within housing 1 that can be chosen for the disposition of sensor 14, such as, for example, a pump housing within housing 1.

Figure 2:
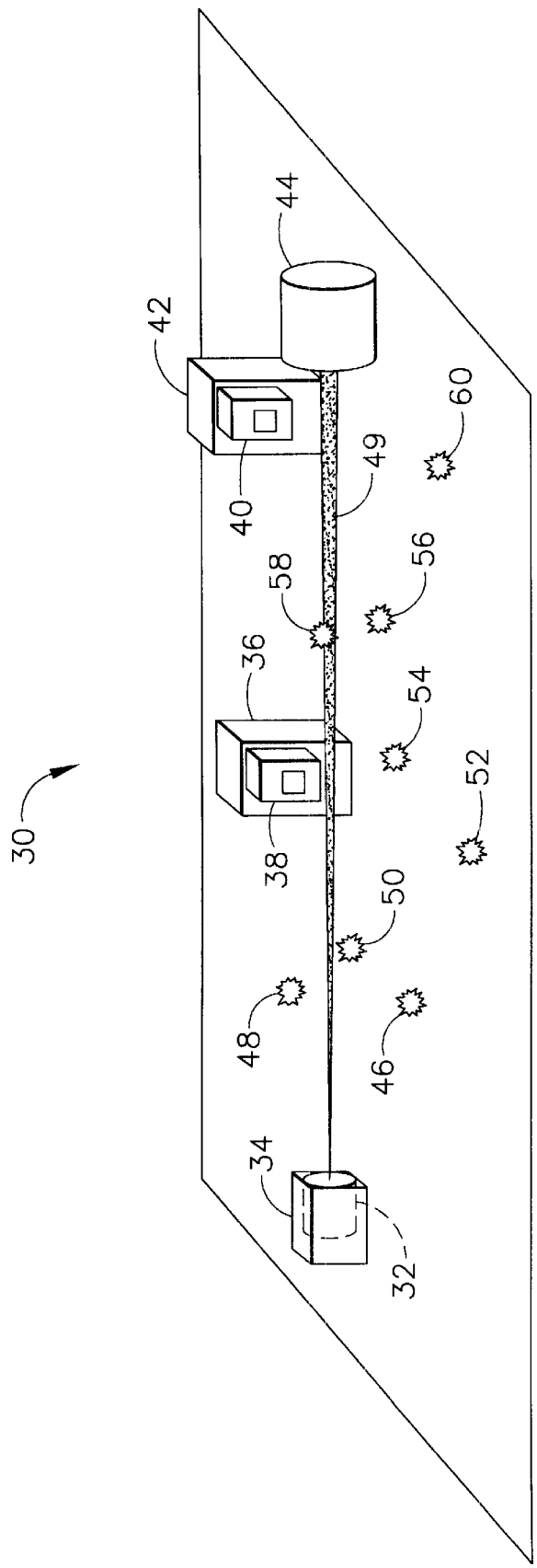
FIG. 2 illustrates a focused laser light turbidity sensor that measures very low concentrations of particles in fluids in accordance with preferred embodiments of the present invention.

FIG. 2 illustrates a focused laser light turbidity sensor 30 that measures very low concentrations of particles in fluids in accordance with preferred embodiments of the present invention. Those skilled in the art can appreciate that the turbidity sensor 30 illustrates one example of a sensor configuration that may be utilized in accordance with the present invention disclosed here, and that additional and varying configurations may be implemented. A laser diode 32 may be utilized as a laser light source for emitting a laser light beam 49. Laser diode 32 thus functions as a lasing device. Laser diode 32 may be contained within a housing 34 that functions as a cavity or cell for maintaining laser diode 32. A variety of particles 46, 48, 50, 52, 54, 56, and 60 are contained within a fluid through which laser light beam 49 passes.

The configuration illustrated in FIG. 2 relies on at least two light-sensitive detectors, which may be semiconductor photodiodes. The laser light beam 49 thus passes through the fluid to be measured. Laser light beam 49 can be emitted as a collimated beam of laser light. Side scatter detector 38 may function as a first light-sensitive detector, while forward scatter detector 40 may function as a second light-sensitive detector. Side scatter detector 38 may be maintained within a cavity, cell or housing 36, and forward scatter detector 40 can be contained within a housing 42. A component 44 for preventing reflection of the incident light beam emitted from laser diode 32 may be positioned opposite laser diode 32. Those skilled in the art can appreciate, based on the foregoing, that in an implementation of the present invention, turbidity information may be obtained from the aforementioned first and second light-sensitive detectors utilizing electrical signal processing, resulting in enhanced information to determine the quality of a measured turbid solution.

Side scatter detector 38, implemented as a semiconductor photodiode, may be located 90 degrees to the incident light beam emitted from laser diode 32 to measure side-scattered light. Forward scatter detector 40 may be positioned at an obtuse angle to the incident light beam (i.e., laser light beam 49) to measure forward-scattered light. Side scatter detector 38 may be moved close to laser light beam 49 to receive maximum scatter signal and yet maintain a low clean-fluid output.

The entire incident light beam (i.e., laser light beam 49), taking into account beam tolerances, may be captured by component 44 that prevents reflection back into the measured fluid. This permits forward-scatter detector 40, including its cavity or housing 42, to be placed as close as possible to laser light beam 49 to thereby provide a maximum signal. The power of the laser light source (e.g., laser diode 32) may be monitored by a detector, not pictured in FIG. 2, located in the vicinity of the light emission to measure the intensity of laser light beam 49, thereby reducing part-to-part variation of the laser light source. As depicted in FIG. 2, the cell or cavity (i.e., housing 36 and 42) may be darkened to eliminate stray or ambient light and undesirable reflections, which can contribute to errors in clean fluid readings. These features can be incorporated into either a flow-through or probe-type package. Those skilled in the art can appreciate that forward-scatter detector 40 can be angled into or toward laser light beam 49 at approximately a 30-degree angle to center of the path of laser light beam 49.

FIG. 3 depicts a high-level block diagram 70 illustrative of a focused laser turbidity sensor that includes a plurality of light-sensitive detectors, in accordance with preferred embodiments of the present invention. Note that in FIGS. 3 to 7, like parts are indicated by like reference numerals. As illustrated in FIG. 3, turbidity sensor may be utilized to measure very low concentrations of particulate in a fluid, such as fluid 74. Such a turbidity sensor can measure a very small amount of particulate in fluids utilizing a focused column of laser light 79. The turbidity sensor illustrated in block diagram 70 can be utilized to measure extremely low levels of contaminates in water purification systems, hydraulic fluids, oils, or other translucent fluids.

Fluid 74 thus may be water utilized in a water purification system, a hydraulic fluid, oil or another type of translucent fluid. Laser light source 72 may be implemented as a low-cost laser diode with a focusing lens to create a focused and strong beam of light (e.g., laser light 79), capable of passing through a wide range of fluids, including washing fluids. Laser light source 72 is unique in turbidity applications because of its focused beam and intense power that can pass through a wide range of turbidity levels in many different solutions. Such a light source, coupled with a specific geometric configuration of light-sensitive detectors can accurately measure very low particulate concentrations in fluids. A plurality of light-sensitive detectors 76 may thus be utilized in association with laser light source 72 and a component 78 or apparatus for preventing the reflection of light back into the measured fluid 74. Note that component 78 of FIGS. 3 to 7 is analogous to component 44 of FIG. 2.

FIG. 4 illustrates a high-level block diagram 80 of a focused laser turbidity sensor that includes first and second light-sensitive detectors, in accordance with preferred embodiments of the present invention. First light-sensitive detector 82 and second light-sensitive detector 84 may be implemented as semiconductor photodiodes.

FIG. 5 depicts a high-level block diagram 90 of a focused laser turbidity sensor that utilizes a Vertical Cavity Surface Emitting Laser (VCSEL) 92 as a laser light source, in accordance with preferred embodiments of the present invention.

A VCSEL is a type of semiconductor laser, which emits light in a direction that is generally perpendicular to an upper surface of the laser structure. Lasers of this type comprise multiple layers of semiconductive material. Typically, a substrate is provided at one end of a stack of semiconductive layers. On the substrate, a first mirror stack and a second mirror stack may be arranged with a quantum well active region therebetween. On both sides of the active region, graded or ungraded layers can be provided as a spacer between mirrors. On the second mirror stack, an electrical contact may be disposed.

Another electrical contact can be provided at the opposite end of the stack of layers in contact with the substrate. An electrical current is caused to flow between the two contacts. This electrical current, therefore, passes through the second mirror stack, a top graded index region, the first mirror stack and the substrate. Typically, a pre-selected portion of the active layer may be designated as the active region and the electrical current is generally caused to flow through the active region in order to induce lasing.

Those skilled in the art can appreciate that the aforementioned description of a typical VSCEL merely represents one type of VCSEL that may be utilized in accordance with preferred embodiments of the present invention. It can be appreciated that a variety of other types of VCSELs may be utilized in accordance with the present invention. The aforementioned general description of a VCSEL is thus presented herein for illustrative purposes only and should not be interpreted as limiting the type of VCSEL utilized in accordance with the invention described herein.

FIG. 6 illustrates a high-level block diagram 100 of a focused laser turbidity sensor that utilizes a light emitting diode (LED) 103 as a light source, in accordance with preferred embodiments of the present invention. LED 103 may be implemented in place of VCSEL 92 of FIG. 5. LEDs are well known in the art and are generally configured as a p-n junction diode that emits light as a result of direct radiative recombination of excess electron-hole pairs known. LEDs are generally utilized for low-voltage display devices, such as electrical watches, but may be implemented as light source in place of focused laser light source 70 of FIGS. 3 and 4. LED 103 should preferably function, however, as a laser light source that emits a focused beam of light through a fluid to be measured. Currently, LEDs do not emit collimated or focused laser light, but it is anticipated that in the future, LEDs may be modified or configured to emit such laser light. Thus, LED 103 may be utilized in association with the present invention described herein, if LED 103 is configured as an LED that emits a focused laser light beam.

FIG. 7 depicts a high-level block diagram 101 of a focused laser turbidity sensor that utilizes side scatter and forward scatter detectors, in accordance with preferred embodiments of the present invention. As indicated above, in FIGS. 3 to FIG. 7, like parts are indicated by identical reference numerals. The turbidity sensor illustrated in block diagram 101 includes a laser light source 72, a side scatter detector 102 and a forward scatter detector 104. Side scatter detector 102 of FIG. 7 is analogous to side scatter detector 38, including housing 36, of FIG. 2. Forward scatter detector 104 of FIG. 7 is analogous to forward scatter detector 40, including housing 42, of FIG. 2.

FIG. 8 depicts a high-level flow chart 110 illustrating operational steps that may be implemented for measuring very low concentrations of particles in fluids, in accordance with preferred embodiments of the present invention. Those skilled in the art can appreciate that flow chart 110 illustrated in FIG. 8 is presented for illustrative purposes only and is not meant to be a limiting feature of the present invention. Other flow charts and methodologies may be followed to implement the turbidity sensor described herein. FIG. 8 depicts one example of a high-level methodology for measuring ultra-low levels of turbidity.

Thus, as illustrated at block 112, a first light sensitive detector may be located 90 degrees to the incident light beam emitted form a laser light source, such as laser light source 72 of FIG. 7, to measure side-scattered light. As indicated next at block 114, a second light sensitive detector may be located at angle obtuse to the incident light beam emitted from the laser light source (e.g., a VCSEL) to measure forward-scattered light. The first light sensitive detector may function as a side scatter detector, as illustrated at block 116. Such a side scatter detector may be moved close to the incident light beam to receive maximum scatter signal and yet maintain a low clean-fluid output. The second light sensitive detector may function as a forward scatter detector, as described at block 118. The forward scatter detector should preferably be placed as close as possible to the incident light beam emitted from the laser light source in order to provide the maximum signal possible. As depicted at block 122, a collimated laser beam may be emitted from the laser light source (e.g., VCSEL). Finally, as illustrated at block 124 light reflected off of particles passing through the laser light beam emitted from the laser light source may be detected and measured through the utilization of the side scatter and forward scatter detectors.

Figures 9, 10:
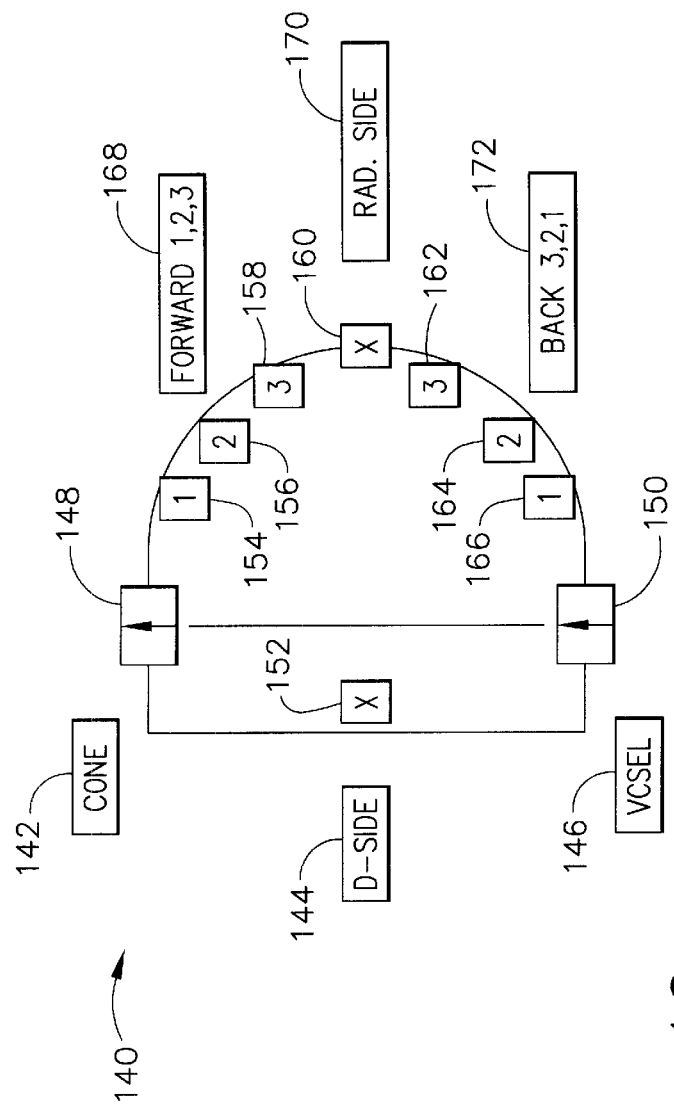
FIG. 9 depicts readings from a D-cell fixture turbidity sensor, in accordance with preferred embodiments of the present invention.
FIG. 10 is a diagram illustrating a D-cell fixture turbidity sensor, in accordance with preferred embodiments of the present invention.

FIG. 9 depicts readings 130 from a D-cell fixture turbidity sensor, in accordance with preferred embodiments of the present invention. Such a D-cell fixture turbidity sensor is illustrated in more detail in FIG. 10. The example illustrated in FIGS. 9 and 10 is based on readings derived from a low NTU turbidity starch investigation. A VCSEL can be utilized as a light source in such an example, with 8 mA of forward current. Solutions to be measured can be based on a potato mix in water. A first potato mix is generally referred to in FIG. 9 as "Potato1". A second potato mix is generally referred to in FIG. 9 as "Potato2". Respective readings are based on d-side, forward1, forward2, forward3, rad. Side, back 3, back 2, and back 1. Those skilled in the art can appreciate that potato-based solutions or other turbid solutions may be prepared for measurement according to the present invention described herein. The readings illustrated in FIG. 9 are thus presented for illustrative purposes only.

FIG. 10 depicts a diagram 140 illustrating a D-cell fixture turbidity sensor, in accordance with preferred embodiments of the present invention. Diagram 140 illustrates a turbidity sensor configuration. Those skilled in the art can appreciate that the configuration illustrated in FIG. 10 represents merely one example of components that may be utilized in a particular turbidity sensor. As illustrated in FIG. 10, a VCSEL 146 is located opposite a diffusing cone 142. A d-side detector 144 is located between cone 142 and VCSEL 146. A forward scatter detector 168 may be located at positions 154, 156 or 158. A radial side detector 170 may be located at position 160. A back scatter detector 172 may be located at positions 162, 164, or 166. D-side detector 144 may be located at position 152. D-side detector 144 may be utilized to monitor the power of VCSEL 146 and may be placed in the vicinity of light emission from VCSEL 146 to measure the intensity of such light emission. This arrangement serves to reduce part-to-part variation of the source. Arrows 150 and 148 indicate the general direction in which light from VCSEL 146 may be emitted.

Figure 11:
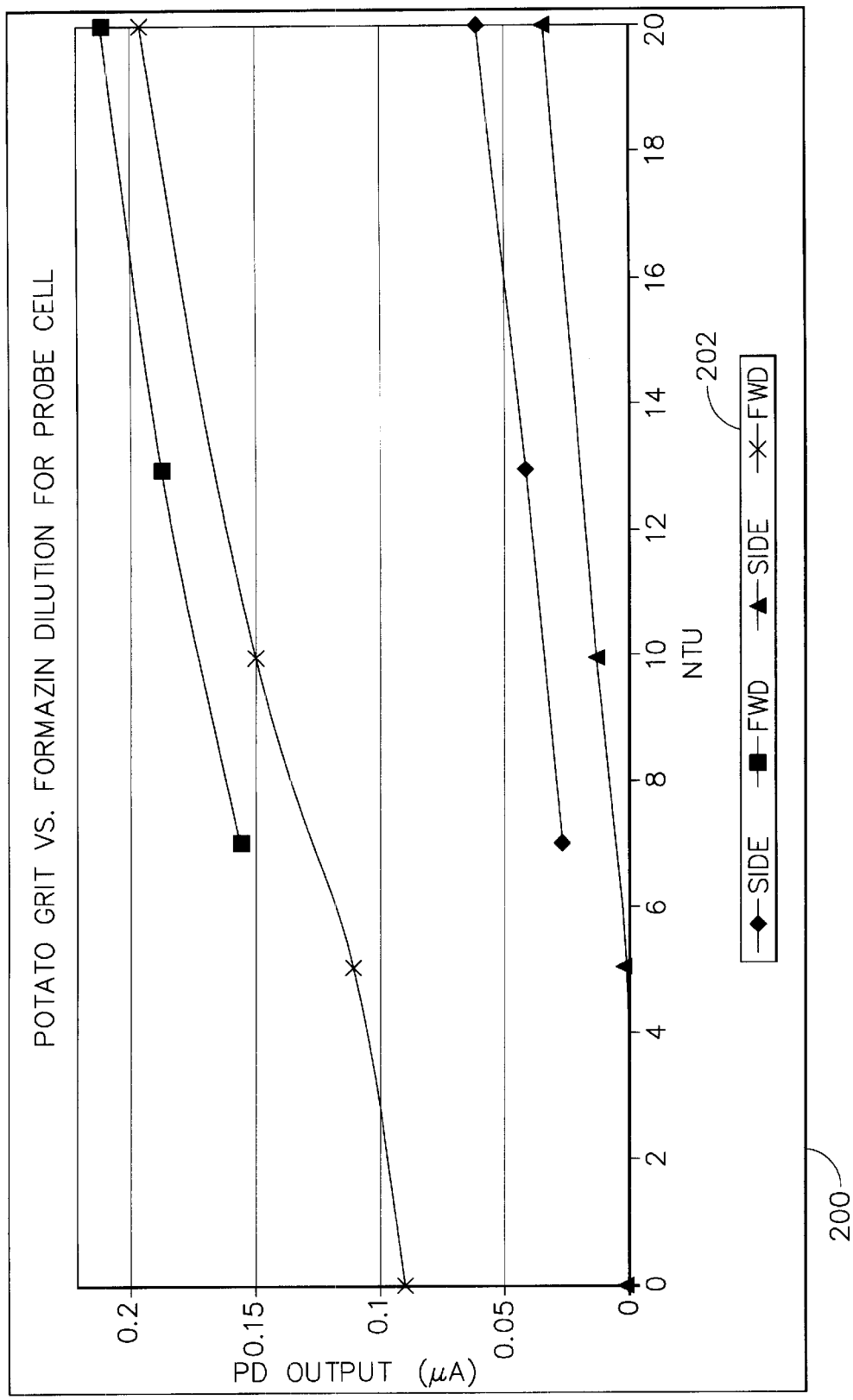
FIG. 11 depicts a plot of readings taken from a probe-type cell fixture turbidity sensor, which may be utilized to implement an embodiment of the present invention.

FIG. 11 depicts a plot 200 of readings taken from a probe-type cell fixture turbidity sensor, which may be utilized to implement an embodiment of the present invention. A legend 202 of the plot indicates line plots associated respectively with a side scatter detector, a forward scatter detector, an additional side scatter detector and an additional forward scatter detector. The readings from plot 200 may be obtained from a probe-type cell fixture loaded with photodiodes in forward and side scatter positions. A VCSEL can be utilized as a light source, powered at 8 mA of forward current. Solutions to be measured may be composed of potato particles mixed with water. A diffusing cone may be utilized in a position opposing the VCSEL. The readings illustrated in plot 200 are generally based on the following data:

Solution#1 measured approximately 7 NTU

Solution#2 measured approximately 13 NTU

Solution#3 measured approximately 20–50 NTU

| | Emitter: VCSEL at 8 mA | | | | |
| --- | --- | --- | --- | --- | --- |
| Position | 7 | 13 | 20 | | |
| Side | 0.027 | 0.041 | 0.06 | | |
| Fwd | 0.155 | 0.186 | 0.21 | | |
| | Original Probe Response | | | | |
| Position | 0 | 5 | 10 | 20 | 50 |
| Side | 0 | 0.001 | 0.012 | 0.033 | 0.091 |
| Fwd | 0.09 | 0.110 | 0.150 | 0.194 | 0.307 |

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

The embodiments of an invention in which an exclusive property or right is claimed are defined as follows:

1. A sensor for measuring low concentrations of particles in a viscous fluid, said sensor comprising:

a VCSEL, wherein said VCSEL emits a laser light beam;

a diffusing cone located opposite said VCSEL that captures incident light from the laser light beam through the viscous fluid and prevents reflection of the incident light back into the viscous fluid;

a side scatter detector contained within a side scatter detector housing and located between said diffusing cone and said VCSEL proximate said laser light beam, wherein said side scatter detector housing is darkened to substantially eliminate ambient light and undesirable reflections, and wherein said side scatter detector monitors power associated with said VCSEL and reduces part-to-part variation of said VCSEL and is located in a vicinity of the incident light to thereby measure an intensity of said laser light beam;

a forward scatter detector that detects forward-scattered light reflected from particles contained within said viscous fluid that come into contact with said laser light beam, wherein said forward scatter detector is located proximate said laser light beam and is contained within a forward scatter detector housing that is darkened to substantially eliminate ambient light and undesirable reflections;

a radial side detector that detects radial-scattered light reflected from particles contained within said viscous fluid that come into contact with said laser light beam, wherein said radial side detector is located proximate said laser light beam; and a back scatter detector that detects back-scattered light reflected from particles contained within said viscous fluid that come into contact with said laser light beam, wherein said back scatter detector is located proximate said laser light beam, such that turbidity information is obtained from said side scatter detector, said forward scatter detector, said radial side detector and said back scatter detector to determine low concentrations of particles within said viscous fluid.

2. The sensor of claim 1 wherein said forward scatter detector is angled toward said laser light beam at approximately a 30 degree angle to a center of a path of said laser light beam.

3. The sensor of claim 1 wherein said side scatter detector is located at approximately 90 degrees to said laser light beam.

4. The sensor of claim 1 wherein said side scatter detector comprises a D-side detector.

5. The sensor of claim 1 wherein said VCSEL comprises a VCSEL powered by at least 8 mA of forward current.

6. The sensor of claim 5 wherein said viscous fluid comprises a solution having a concentration of approximately 7 NTU.

7. The sensor of claim 5 wherein said viscous fluid comprises a solution having a concentration of approximately 13 NTU.

8. The sensor of claim 5 wherein said viscous fluid comprises a solution having a concentration of approximately 20 NTU to 50 NTU.

9. The sensor of claim 1 wherein said sensor comprises a probe-type cell fixture sensor.

10. A sensor for measuring low concentrations of particles in a viscous fluid, said sensor comprising:

a VCSEL, wherein said VCSEL emits a laser light beam through said viscous fluid;

a diffusing cone, located opposite said VCSEL, that entirely captures incident light from the laser light beam emitted from the VCSEL through said viscous fluid and prevents reflection of said light back into said viscous fluid;

a side scatter detector contained within a side scatter detector housing and located between said diffusing cone and said VCSEL proximate said laser light beam, wherein said side scatter detector housing is darkened to substantially eliminate ambient light and undesirable reflections, and wherein said side scatter detector monitors power associated with said VCSEL and reduces part-to-part variation of said VCSEL and is located in a vicinity of light to thereby measure an intensity of said laser light beam, wherein said side scatter detector is located approximately 90 degrees to said laser light beam;

a forward scatter detector that detects forward-scattered light reflected from particles contained within said viscous fluid that come into contact with said laser light beam, wherein said forward scatter detector is located proximate said laser light beam and is contained within a forward scatter detector housing that is darkened to substantially eliminate ambient light and undesirable reflections, wherein said forward scatter detector is angled into said laser light beam at approximately a 30 degree angle to a center of a path of said laser light beam;

a radial side detector that detects radial-scattered light reflected from particles contained within said viscous fluid that come into contact with said laser light beam, wherein said radial side detector is located proximate said laser light beam; and a back scatter detector that detects back-scattered light reflected from particles contained within said viscous fluid that come into contact with said laser light beam, wherein said back scatter detector is located proximate to said laser light beam, such that turbidity information is obtained from said side scatter detector, said forward scatter detector, said radial side detector and said back scatter detector to determine low concentrations of particles within said viscous fluid.

11. A method for measuring low concentrations of particles in a viscous fluid, said method comprising the steps of:

locating a diffusing cone opposite a VCSEL such that said diffusing cone entirely captures incident light from a laser light beam emitted from said VCSEL through said viscous fluid and prevents reflection of said light back into said viscous fluid;

positioning said VCSEL opposite said diffusing cone such that said VCSEL emits the laser light beam from said VCSEL to said diffusing cone through said viscous fluid;

locating a side scatter detector contained within a side scatter detector housing between said diffusing cone and said VCSEL and proximate said laser light beam, wherein said side scatter detector housing is darkened to substantially eliminate ambient light and undesirable reflections, and wherein said side scatter detector monitors power associated with said VCSEL and reduces part-to-part variation of said VCSEL and is located in a vicinity of said laser light beam to thereby measure an intensity of said laser light beam;

positioning a forward scatter detector contained within a forward scatter detector housing darkened to substantially eliminate ambient light and undesirable reflections proximate said laser light beam, wherein said forward scatter detector detects forward-scattered light reflected from particles contained within said viscous fluid that come into contact with said laser light beam;

locating a radial side detector proximate said laser light beam, wherein said radial side detector detects radial-scattered light reflected from particles contained within said viscous fluid that come into contact with said laser light beam; and positioning a back scatter detector proximate said laser light beam, wherein said back scatter detector detects back-scattered light reflected from particles contained within said viscous fluid that come into contact with said laser light beam, such that information is obtained from said side scatter detector, said forward scatter detector, said radial side detector and said back scatter detector to determine low concentrations of particles within said viscous fluid.

12. The sensor of claim 11 further comprising the step of:

configuring said forward scatter detector, such that said forward scatter detector is angled toward said laser light beam at approximately a 30-degree angle to a center of a path of said laser light beam.

13. The sensor of claim 11 further comprising the step of:
configuring said side scatter detector, such that said side scatter detector is located at approximately 90 degrees to said laser light beam.

14. The method of claim 11 wherein said side scatter detector comprises a D-side detector.

15. The method of claim 11 wherein said VCSEL comprises a VCSEL powered at least 8 mA of forward current.

16. The method of claim 15 wherein said viscous fluid comprises a solution having a concentration of approximately 7 NTU.

17. The method of claim 15 wherein said viscous fluid comprises a solution having a concentration of approximately 13 NTU.

18. The method of claim 15 wherein said viscous fluid comprises a solution having a concentration of approximately 20 NTU to 50 NTU.

19. The method of claim 11 wherein said sensor comprises a probe-type cell fixture sensor.

20. The method of claim 11 further comprising the step of:
locating at least one additional forward scatter detector contained within a forward scatter detector housing darkened to substantially eliminate ambient light and undesirable reflections proximate said laser light beam, wherein said at least one additional forward scatter detector detects forward-scattered light reflected from particles contained within said viscous fluid that come into contact with said laser light beam.

* * * * *